United States Patent [19]

Herr et al.

[11] Patent Number: 4,735,898
[45] Date of Patent: Apr. 5, 1988

[54] MONOCLONAL ANTIBODIES AND METHOD OF IDENTIFYING SPECIES USING THE SAME

[75] Inventors: John C. Herr; David C. Benjamin, both of Charlottesville, Va.

[73] Assignee: The University of Virginia Alumini Patents Foundation, Charlottesville, Va.

[21] Appl. No.: 755,564

[22] Filed: Jul. 16, 1985

[51] Int. Cl.$^4$ ............... G01N 33/53; G01N 33/577; C12N 15/00
[52] U.S. Cl. ............................... 435/7; 435/13; 435/68; 435/240.27; 435/810; 436/547; 436/548; 436/518; 436/528; 436/808; 436/810; 935/103; 935/104; 935/105; 935/110
[58] Field of Search ............... 530/387, 809; 935/89, 935/103-105, 110; 435/7, 13, 68, 172.2, 240, 241, 810, 240.27; 436/547, 548, 808, 810, 518, 528

[56] References Cited

FOREIGN PATENT DOCUMENTS 60-258128A 12/1985 Japan .................................. 435/240
8300048 1/1983 Int. Prop. O. ..................... 435/240

OTHER PUBLICATIONS

Fletcher et al, Chemical Abstracts, 100(1984) 115935, Abstracting J. Forensic Sci. 1984, 29(1) 67–74.
Watanabe et al, Chemical Abstracts, 103(1985) 99821y Abstracting Kanagawa Keisatsu Kenkyusho Hokoku, Hokagaku Hen, 1984, 37(3) 169–75 (Japan).
Lapresle et al, Molecular Immunology, vol. 20(5), pp. 549–555 (1983).
Doyen et al, Molecular Immunology, vol 22(1), pp. 1–10 (1985).
Hosoi et al, Clinical Immunological Immunopathology, vol. 32(3), Abstract only (1984).

Primary Examiner—Christine M. Nucker
Attorney, Agent, or Firm—James Creighton Wray

[57] ABSTRACT

The new method an products recognize human serum albumin, differentiating blood and tissue from human sources from blood and tissue of other animals. The method and products are particularly useful in forensic investigations. First, mice are injected with purified human serum albumin, spleen cells from the mice are fused with cells from a murine myeloma. Resulting hyberdomas are screened on human serum albumin coated plates. Subcloning, stabilizing by culture and continued assays for anti-human albumin activity produces products which recognize and differentiate blood or tissue samples from samples of other species.

11 Claims, No Drawings

MONOCLONAL ANTIBODIES AND METHOD OF IDENTIFYING SPECIES USING THE SAME

BACKGROUND OF THE INVENTION

The use of polyclonal antisera to distinguish between species based on unique structural domains of serum proteins has been utilized by the forensic community since the turn of the century. In current forensic practice tests employing such methods as immunoprecipitation, antibody coated latex spheres, or immunodiffusion rely on high quality, carefully tested antisera which have been extensively cross absorbed to eliminate cross reactivity. Such cross reactivity of polyclonal antisera with serum proteins of closely related species is the major limitation of current tests for species of origin in the forensic art. Depending on the discriminatory capability of the polyclonal antiserum in a given method, the phylogenetic relationships between related species impose intrinsic limits on the ability to differentiate related blood or tissue specimens. As Sensabaugh has noted, medico-legal tests would be far more satisfactory if monospecific antisera to rapidly evolving (widely divergent) blood marker proteins were employed, thereby taking advantage of greater differences in the structure of similar proteins, even in closely related species.

Serum albumin has such a potential to be a forensic marker protein because it shows considerable phylogenetic divergence as evidenced by both amino acid sequence data and immunological cross reactivity. Albumins from thousands of pairs of vertebrate species have been compared immunologically and the results have been used to establish approximate time scales for genealogical trees by which these species are related, thereby permitting a quantitative approach to the study of evolution.

A vast literature which spans three decades has demonstrated that serum albumin is a multideterminant antigen.

Recent studies using monoclonal antibodies produced to bovine serum albumin have shown a minimum of 25 different determinants to be present in a panel of 10 mammalian albumins.

At least 13 of these epitopes are non overlapping determinants which are not repeated on subdomains of the albumin molecule. This evidence for the existence of multiple determinants on the albumin molecule provides the rationale for use of monoclonal antibodies to human serum albumin for identification of human tissue and blood in forensic studies.

SUMMARY OF THE INVENTION

In this patent application we report the characterization of monoclonal antibody designated HB8860 by The American Type Culture Collection which shows specificity for a unique epitope on human serum albumin. We describe a sensitive ELISA assay which has been developed using this monoclonal antibody. Further, the application of this assay on forensic casework is reported.

The monoclonal antibody, has been checked for cross reactivity with albumin samples obtained from orangutan, gorilla, rat, bovine, goat, sheep, pig, deer, rabbit, dog, and cat and has been found not to cross react. Its specificity for human albumin makes this clone of potential use in assays of blood and/or tissue specimens samples of unknown origin to identify whether the sample is from a human. This monoclonal antibody, employed in an enzyme linked immunosorbent assay (ELISA) or other type of assay kit, might become the assay of choice in crime laboratories. The serological determination of the species of origin is one of the most frequently required tests performed by the forensic serologist on blood samples. Such an assay based upon a monoclonal antibody provides all the advantages of monoclonal immunoreagents, including specificity, constant avidity an affinity, and a virtually unlimited supply; making adoption of such a clone as a national standard an important consideration.

The monoclonal antibody, was produced by fusing spleen cells from Balb/c (A/J) mice, injected with purified human serum albumin, to a murine myeloma (SP2/0). The monoclonal antibody was selected by screening resulting hybridomas on human serum albumin coated plates; and then was subcloned and stabalized by several months of culture and continued assay for anti albumin activity. The monoclonal antibody is isotyped as an IgG (k).

The specificity of the monoclonal antibody for human albumin was established by cross reactivity studies on purified albumins from orangutan, gorilla, rat, bovine, goat, sheep, pig, deer, rabbit, dog, and cat. The antibody did not recognize albumins from these species.

The antibody has undergone testing on blood samples from a variety of species and has consistently been able to select out those samples of human origin.

An assay system for human albumin using this monoclonal antibody should provide a valuable tool for the forensic community.

DETAILED DESCRIPTION OF A PREFERRED EMBODIMENT

1. Hybridoma Production:

Balb/c mice were injected three times with human serum albumin (Fraction V powder in PBS; Pentex, Miles Laboratories) i.p. spaced two weeks apart. The first injection was in Complete Freunds Adjuvant, and the next two in Incomplete FA. Each injection contained 500 $\mu$g HSA. The mice were rested for 30 days later, spleen cells from the immunized mice were fused with SP2/0 myeloma cells using PEG.

2. Albumin Purification:

Serum was precipitated with an equal volume of saturated ammonium sulfate, pH 7.0. The supernatant was harvested and the pH adjusted slowly to 4.4. The precipitate formed was dissolved in water and dialysed against saline. This step was repeated two times, then the final precipitate was dissolved and dialysed and then run on an Afigel Blue (Biorad) column as a final purification step.

The following solutions were prepared for use in the assay.

| Solution A (pH 9.6) | | |
|---|---|---|
| Sodium bicarbonate | NaHCO$_3$ | 1.59 g/l |
| Sodium carbonate (anhydrous) | Na$_2$CO$_3$ | 2.96 g/l |
| Solution B (pH ~7.4) | | |
| Sodium chloride | NaCl | 8.0 g/l |
| Potassium phosphate | K$_2$HPO$_4$ | 0.20 g/l |
| Sodium phosphate (dibasic; anhydrous) | Na$_2$HPO$_4$ | 1.15 g/l |
| Potassium chloride | KCl | 0.20 g/l |
| Tween 20 | | 1.0 ml/l |
| Thimersol | | 0.10 g/l |
| Solution C (pH 8.0) | | |
| Sodium phosphate (dibasic; | Na$_2$HPO$_4$ | 2.825 g/l |

-continued

| | | |
|---|---|---|
| anhydrous) | | |
| pH to 8.0 with hydrochloric acid | | |
| Solution D (pH 6.8 to 7.2) | | |
| Sodium chloride | NaCl | 8 g/l |
| Sodium phosphate (monobasic) | $NaH_2PO_4 \cdot H_2O$ | 1.4 g/l |
| pH to correct range with Sodium hydroxide. | | |
| Solution E (pH 4.2) | | |
| Citric acid (anhydrous) | $H_2C_6H_5O_7$ | 5.64 g/l |
| Sodium phosphate (dibasic; anhydrous) | $Na_2HPO_4$ | 5.84 g/l |
| When ready to use add 1 mM ABTS (2,2' azino-di-(3-ethylbenzthiozoline sulfonic acid) and 0.03% hydrogen peroxide ($H_2O_2$) [1 mM ABTS = 0.055 g ABTS/100 ml buffer; 0.03% $H_2O_2$ = 1 µl 30% $H_2O_2$/1 ml buffer] | | |
| Solution F | | |
| Citric acid (anhydrous) | $H_2C_6H_5O_7$ | 1.92 g/100 ml |
| Sodium azide | $NaN_3$ | 0.01 g/100 ml |
| Solution G (pH ~3.0) | | |
| Citric acid (anhydrous) | $H_2C_6H_5O_7$ | 3.84 g/100 ml |

PREPARATION OF FORENSIC SAMPLES (1) Place cloth sample in tube and add 0.5 ml solution D. Incubate 30 minutes at 37 degrees Celsius.
(2) Spin tubes and pull off supes to use.
(3) Dilute 1:20 in 1% ovalbumin in solution D.
(4) Use 50 µl/well in assay, and store unused portion at −20 degrees Celsius.
This may need to be modified depending on nature of sample. As written for cloth samples.

Specificity Assay (1) Coat plates (Immulon II) with albumins at 50 µg/ml in solution A. Use 50 µl/well and incubate either 1 hour at 37 degrees Celsius or overnight at 4 degrees Celsius. All incubations should be in a humid chamber.
(2) Wash plates 4X. All washes are done in solution B.
(3) Saturate plates with 0.1% gelatin in solution D using 200 µl/well. Incubate 30 minutes at 37 degrees Celsius.
(4) Wash 4X with solution B.
(5) Add monclonals to plate at 50 µg/ml in solution C. Use 50 µl/well and incubate 1 hour at 37 degrees Celsius.
(6) Wash 4X with solution B.
(7) Add Horseradish peroxidase conjugated antimouse gama globulin (HRP-RxMGG) diluted 1:1000 in solution D. (Antibody has been absorbed on mouse serum; see attached procedure). Use 50 µl/well and incubate 1 hour at 37 degrees Celsius.
(8) Wash 4X with solution B.
(9) Add solution E (substrate) at 100 µl/well. Incubate at room temperature for 5–15 minutes until color develops.
(10) Stop reaction by adding 50 µl/well of solution F.
(11) Read on Multiscan at 415 nm.

Forensic Assay (1) Coat plates (Immunlon II) with monclonals at 50 µl/well in solution C at the following concentrations:
A Bovine Serum Albumin 50 µg/ml
A Deer Serum Albumin 20 µg/ml
A Human Serum Albumin 50 µg/ml
Incubate 1 hour at 37 degrees Celsius or overnight at 4 degrees Celsius. All incubations should be in a humid chamber.
(2) Wash plates 4X. All washes are done in solution B.
(3) Saturate plates with 0.1% gelatin in solution D using 200 µl/well. Incubate 30 minutes at 37 degrees Celsius.
(4) Wash 4X in solution B.
(5) Add prepared forensic samples and control albumins. Control albumins (BSA, DSA, and HSA) are at 50 µg/ml in 1% ovalbumin in solution D. Add 50 µl/well of each sample or control to each anti-albumin plate. Incubate 1 hour at 37 degrees Celsius.
(6) Wash 4X in solution B.
(7) Add 3% $H_2O_2$ in solution D to sample wells only (100 µl/well). Incubate 30 minutes at 37 degrees Celsius.
(8) Wash 8X in solution B.
(9) Prepare a mixture of rabbit anti-albumin as follows: 12.5 pl anti-BSA plus 2.5 µl anti-HSA (both preabsorbed on NMS column) are added to 5 ml solution D. This gives a final dilution of 1:400 and 1:2000 respectively.
(10) Add 50 µl of this mixture to each well. Incubate at 37 degrees Celsius for one hour.
(11) Wash 4X in solution B.
(12) Horseradish peroxidase conjugated goat antirabbit gamma globulin (HRP-GxRGG) is diluted 1:1000 in solution D. (Antibody absorption mouse serum). Add 50 µl/well and incubate 1 hour at 37 degrees Celsius.
(13) Wash 4X in solution B.
(14) Add 100 µl Solution E (substrate) to each well. Incubate at room temperature for 5–15 minutes until color develops.
(15) Stop reaction by adding 50 µl/well of solution F.
(16) Read on Multiscan at 415 nm.

Results:

1. Table 1 gives absorbance readings indicating specificity of the HSA-1 monoclonal for human albumin and lack of cross reactivity with albumins of 11 other species.

TABLE 1

| Cross Reactivities of UVA-Anti HSA-1 with a Panel of Albumins. | | | | | |
|---|---|---|---|---|---|
| Albumin | Anti-BSA | Anti-DSA | Anti-HSA | Gel | Anti-HSA-Gel |
| Bovine | 1.599 | 0.162 | 0.126 | 0.125 | 0.001 |
| Deer | 0.550 | 1.515 | 0.127 | 0.130 | 0.000 |
| Dog | 1.183 | 0.180 | 0.123 | 0.087 | 0.046 |
| Goat | 0.650 | 0.132 | 0.091 | 0.109 | 0.000 |
| Gorilla | 0.464 | 0.017 | 0.024 | 0.043 | 0.019 |
| Horse | 0.543 | 0.051 | 0.019 | 0.000 | 0.019 |
| Human | 0.440 | 0.145 | 1.083 | 0.098 | 0.985 |
| Orangutan | 1.106 | 0.143 | 0.100 | 0.094 | 0.006 |
| Porcine | 0.548 | 0.145 | 0.135 | 0.186 | 0.000 |
| Rabbit | 0.526 | 0.162 | 0.125 | 0.139 | 0.000 |
| Rat | 0.625 | 0.158 | 0.131 | 0.168 | 0.000 |
| Sheep | 0.738 | 0.121 | 0.104 | 0.097 | 0.007 |

2. Thirty-one forensic samples provided by the FBI were assayed using the HSA monclonal at UVA. Another thirty forensic samples, provided by the FBI, were assayed during a workshop at the FBI Training Academy. The ELISA assay employing the UVA-HSA-1 monoclonal was able to discriminate those samples containing human blood.

The monoclonal antibody UVA-HSA-1 is able to discriminate between albumins from 11 different species by showing specificity for human albumin. It has been applied to presumptive blood stains and been shown to be effective as a forensic probe for determination of the species of origin of a blood sample.

We claim:

1. Hybrid cell line ATCC No. 8860 secreting monoclonal antibodies specifically reactive with human serum albumin.

2. Monoclonal antibodies secreted by the hybrid cell line of claim 1.

3. A method of identification of species of origin of blood, bloodstain, or tissue sample comprising contacting a sample containing albumin with anti-albumin monoclonal antibodies specific to a particular species and sensing reactivity of the monoclonal antibody with the albumin from the sample.

4. The method of claim 3 wherein the albumin is from the human species and wherein the contacting comprises contacting the albumin with human anti-albumin.

5. The method of claim 4 further comprising the preliminary steps of preparing the sample by isolating albumin from the sample.

6. The method of claim 4 comprising placing the monoclonal antibodies on a plate means and adding the sample to the substrate.

7. The method of claim 5 further comprising placing the albumin from the sample on the plate means and adding the monoclonal antibodies to the substrate.

8. The method of claim 4 wherein the sensing reactivity comprises sensing absorption readings which indicate specificity of the monoclonal antibodies for human albumin.

9. A forensic kit for identification of human species of blood, bloodstain, or tissue samples comprising human anti-albumin monoclonal antibodies, plate means for containing the monoclonal antibodies with albumin from a sample, enzyme and substrate for indicating the reactivity of the monoclonal antibodies with albumin from the sample.

10. The method of claim 3 wherein the monoclonal antibody is ATCC No. HB 8860.

11. The kit of claim 9 wherein the monoclonal antibody is ATCC No. HB 8860.

* * * * *